(12) United States Patent
Joziak et al.

(10) Patent No.: US 6,361,761 B1
(45) Date of Patent: Mar. 26, 2002

(54) FOAMABLE DENTAL FLUORIDE COMPOSITION

(75) Inventors: Marilou T. Joziak, South River; Edward A. Tavss, Kendall Park; Steven W. Fisher, Middlesex; Robert J. Gambogi, Belle Mead, all of NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/543,232

(22) Filed: Apr. 5, 2000

(51) Int. Cl.$^7$ .................. A61K 7/18; A61K 33/16
(52) U.S. Cl. .................. 424/52; 424/45; 424/673; 424/676; 433/215; 433/217.1
(58) Field of Search .................. 424/49, 55–58, 424/45, 673, 676

(56) References Cited

U.S. PATENT DOCUMENTS

| | | | | |
|---|---|---|---|---|
| 4,223,003 A | * | 9/1980 | Scheller | 424/49 |
| 4,568,540 A | * | 2/1986 | Asano et al. | 424/52 |
| 4,770,634 A | * | 9/1988 | Pellico, I | 433/217.1 |
| 4,828,849 A | * | 5/1989 | Lynch | 424/52 |
| 5,071,637 A | * | 12/1991 | Pellico, II | 424/45 |
| 5,073,363 A | * | 12/1991 | Pellico, III | 424/49 |
| 5,275,805 A | * | 1/1994 | Nabia et al. | 424/54 |
| 5,599,526 A | * | 2/1997 | Viscio, I et al. | 424/49 |
| 5,723,105 A | * | 3/1998 | Viscio, II et al. | 424/49 |
| 5,824,289 A | * | 10/1998 | Stolz | 424/45 |

\* cited by examiner

Primary Examiner—Shep K. Rose
(74) Attorney, Agent, or Firm—Paul Shapiro

(57) ABSTRACT

A dental fluoride foam composition comprising a foamable fluoride containing composition that is packaged in a foam generating container, the composition being comprised mainly of, an aqueous solution of a water soluble fluoride ion releasable salt, a taurate surfactant whereby the composition when dispensed from the container into the trough of a dental tray forms a low density, rapidly collapsible foam which substantially liquefies in about 1 minute after being dispensed from the foam generating container and placed in contact with a patients teeth.

6 Claims, No Drawings

FOAMABLE DENTAL FLUORIDE COMPOSITION

FIELD OF THE INVENTION

The present invention relates to an improvement in the reduction of dental caries by the use of a fluoride containing dental foam and more particularly with a low density, dental fluoride aerosol foam which collapses readily on contact with the teeth.

BACKGROUND OF THE INVENTION

Effective medical management of dental caries is required for populations of patients that exhibit increased risk factors for caries. It is known that the presence of dental caries in certain patient subpopulations accounts for substantial proportion of the dental caries seen in the population at large. Reports exist indicating that 25% of the US children account for 75% of dental caries.

One present practice to reduce dental caries in children is the periodic application, e.g., 1 to 2 times per year, of a foamable fluoride composition having a relatively high concentration of a fluoride releasing salt, e.g., 1–3% by weight such as sodium fluoride, which is packaged in an aerosol container in combination with an aerosol propellant. The composition is dispensed from the container into the trough of a dental tray as a dense, stable, non-flowable foam which is superimposed about and into engagement with the teeth to be treated to thereby affect fluoride uptake by the dental enamel.

Although the dental foams, as for example, those disclosed in U.S. Pat. No. 4,770,634, U.S. Pat. No. 5,071,637 and U.S. Pat. No. 5,073,363 are effective and are in present commercial use, in practice, the thick, dense foam that is produced creates problems of fullness discomfort being experienced in the patients mouth. When the treatment is completed, that is, within about one minute of tooth contact, the residual dense foam is difficult to remove from the patients mouth and requires a protracted amount of time to aspirate the residual foam. The problems encountered with the dense foam tend to discourage professional usage and patient compliance with the fluoride treatment.

Therefore, what is needed in the art is an improved dental fluoride foam composition for the treatment of tooth surfaces which facilitates professional usage and patient compliance so that treatment can be repeated over time to provide effective fluoride treatment for dental caries.

SUMMARY OF THE INVENTION

In accordance with the present invention there is provided a low density, foamable fluoride composition packaged in a foam generating container, the composition comprised mainly of an aqueous solution of a water soluble fluoride ion releasable salt, a taurate surfactant and an orally compatible acidifying agent in an amount sufficient to adjust the pH of the composition to about 3 to 5.

In use, the composition is dispensed from the foam generating container into the trough of a dental tray to form a low density, fluoride foam within the trough, which is then superimposed about and into engagement with the teeth of the patient undergoing fluoride treatment.

The low density foam of the present invention rapidly collapses on contact with the patients teeth and does not present a feeling of fullness in the mouth as that experienced with high density dental fluoride foams of the prior art. The low density foam of the present invention breaks up or collapses upon contact with the teeth in a sufficiently short period of time so that it can be discarded substantially in liquid form from the dental tray trough as well as easily rinsed and removed from the patients mouth.

The term "collapsible foam" as it is used in the present application means a foam that collapses, i.e., becomes substantially liquid in a period of about 1 minute after its formation in the dental tray trough and placement on the patients teeth. After this short period of time, the aerosol foam is substantially collapsed to a liquid and the patients teeth is simply rinsed free of the residual foam.

In contrast with commercial dental foams of the prior art wherein the foam is dense and maintained for a significant period of time, it is the rapidly defoaming or collapsing characteristic of the foams produced from the subject compositions that is responsible for its advantageous benefit of mouth acceptability easy removal from the patients teeth.

DETAILED DESCRIPTION OF THE PREFERRED EMBODIMENTS

Examples of water soluble fluoride ion releasable salts useful in the practice of the present invention include sodium fluoride and sodium monofluorophosphate. The fluoride ion is present in the foamable composition of the present invention at a concentration of about 0.5 to about 3.5% by weight and preferably about 1 to about 1.5% by weight.

The term "taurate surfactant" as used in the present specification is a surfactant which is a N-acyl N-alkyl taurate alkali metal salt. A preferred taurate surfactant is available from Finetex Inc., as Tauranol RTM WHSP having the formula:

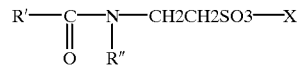

wherein R' is cocoyl, R" is methyl and X is sodium.

However, more generally, X can be alkali metal such as sodium, magnesium or potassium (and including functionally equivalent ammonium), R' is an alkyl group with C8–18 linear hydra-carbon chain length, preferably C12–16 and R" is a C1–4 n-alkyl group, preferably methyl.

Representative taurate surfactants include the sodium, magnesium and potassium salts of N-cocoyl-N-methyltaurate, N-palmitoyl-N-methyl-taurate and N-oleyl-N-methyl taurate and their lauroyl, myristoyl, stearoyl, ethyl, n-propyl and n-butyl homologs.

The taurate surfactant is present in the composition of the present invention in an amount between about 0.1 and about 3% by weight and preferably about 0.6 to about 1.5% by weight.

Acidifying agents useful in the practice of the present invention include inorganic acids such as phosphoric acid, hydrochloric acid and hydrofluoric acid and organic acids such as hydroxysuccinic acid, citric acid and tartaric acid and mixtures thereof. The acidifying agent is present in the foamable composition in an amount ranging from about 0.5 to about 3.5% by weight to adjust the pH to between about 3 to about 5.

A buffering salt such as sodium hydrogen phosphate is included in the compositions of the present invention to inhibit tooth demineralization exposed to the acidified foam.

The propellants used in the pressurized aerosol container in which the foamable composition of the present invention maybe packaged are selected from among hydrocarbon gases such as isobutane, propane and mixtures thereof. A particularly preferred propellant consists of an 80/20 isobutane/propane mixture such as the product sold by Diversified CPC under the name "Aeron A-46". The propellant is present in the pressurized container in proportions of the order of 5–20% by weight relative to the total weight of the composition and preferably 7 to 10%.

The rapidly collapsible fluoride dental foams according to the present invention generally contain a sweetening agent at concentrations which may range between 0.1 and 1%, preferably between 0.25 and 0.35% relative to the total weight to of the composition. Among these agents, sodium saccharinate may be mentioned by way of example. The foams may also contain preservatives such as sodium benzoate, methyl para-hydroxybenzoate, propyl para-hydroxybenzoate and the like in quantities of between 0.01 and 0.5% by weight relative to the total weight of the composition. A flavoring substance in proportions of preferably between 0.5 and 5% relative to the total weight of the foam expelled from the aerosol device is generally present in the composition. Oils of mint (curly mint or peppermint), aniseed, eucalyptus, cinnamon, clove, sage and liquorice and fruit essences such as oils of lemon, orange, mandarin and strawberry are illustrative of flavoring substances useful in the practice of the present invention.

The foamable fluoride compositions of the present invention are prepared by blending the fluoride salt and acidifying agent with taurate surfactant, sweetening agent, flavor and preservative in an aqueous solution. The resulting aqueous solution, containing about 90 to about 98% by weight water, and preferably about 92 to about 95% by weight water, is added in a predetermined amount to a foam generating container. For an aerosol container, an appropriate aerosol valve is securely fitted to the mouth of the container. The container is then charged through the aerosol valve with an aerosol propellant of about 4% to 10%, preferably 7% of the relative fill weight of the aerosol container. A dispensing actuator and spout assembly is then fitted onto the valve.

In use, the foam generating container, is rotated to align the dispensing spout with the trough of a dental tray and the actuator is pressed to dispense an amount of fluoride foam that substantially fills the volume defined by the trough. The tray is then placed in a patients mouth so as to superimpose the trough and its fluoride foam content about and into engagement with the teeth to be treated. The fluoride foam is maintained in engagement with the teeth for about 1 to 4 minutes to effect the fluoride treatment of the teeth.

The foam that is formed in the trough is "fluffy", with a relatively light body, as distinguished from the dense foams of the prior art and collapses readily so as to allow for quick and easy removal of the residual treatment foam by simple aspiration or water rinsing of the mouth.

The following example is illustrative of the present invention and is not to be construed as a limitation of the invention as many variations are possible without departing from its spirit and scope.

EXAMPLE

A foamable fluoride treatment composition having the ingredients listed in the Table below was prepared by dissolving the ingredients in water, in the order listed, at room temperature.

TABLE

| Ingredient | % by Weight |
|---|---|
| Deionized water | 92.95 |
| Sodium fluoride | 2.72 |
| Sodium benzoate | 0.10 |
| Sodium phosphate monobasic | 1.38 |
| Sodium saccharin | 0.250 |
| Hydrochloric acid | 1.00 |
| Tauranol* | 1.00 |
| Flavor - mint | 0.60 |
| Total | 100.000 |

*Sodium methyl cocoyl taurate

One hundred thirty nine and one half (139.5)grams of the treatment composition and then 10.5 grams of Aeron A-46 a 80/20 mixture of isobutane and propane were introduced into an aerosol container equipped with a valve and directory nozzle. A dental foam dispensed from the container collapsed within 1 minute after being dispensed into the trough of a dental tray and placed in contact with a patients teeth. Upon collapse of the foam the tray was removed form the patient's mouth and any residual foam was removed by simple water rinsing of the patient's mouth.

What is claimed is:

1. A low density foamable dental fluoride foam composition comprising a foamable fluoride containing composition that is packaged in a foam generating container, the composition consisting essentially of an aqueous solution of a water soluble fluoride ion releasable salt, a taurate surfactant and an orally compatible acidifying agent in an amount sufficient to adjust the pH of the composition to about 3 to about 5 whereby the composition when dispensed from the container into the trough of a dental tray forms a low density, rapidly collapsible foam which substantially liquefies in about 1 minute after being dispensed from a foam generating container and placed in contact with a patients teeth, from which it can be readily rinsed and removed from the patients mouth.

2. The dental foam of claim 1 wherein the taurate surfactant is sodium methyl cocoyl taurate.

3. The dental foam of claim 1 wherein the fluoride salt is sodium fluoride.

4. The dental foam of claim 1 wherein the foam generating container is an aerosol container.

5. The dental foam of claim 4 wherein the aerosol container is charged with a hydrocarbon gas.

6. The dental foam of claim 5 wherein the hydrocarbon gas is a mixture of isobutane and propane.

* * * * *